United States Patent
Gainor et al.

(10) Patent No.: US 7,033,393 B2
(45) Date of Patent: Apr. 25, 2006

(54) SELF-TRANSITIONING SPINAL DISC ANULUS OCCULSION DEVICE AND METHOD OF USE

(75) Inventors: John Gainor, White Bear Township, MN (US); Britt K. Norton, Eden Prairie, MN (US); Orson James May, Macon, GA (US); Anthony C. Phillips, Eden Prairie, MN (US)

(73) Assignee: Raymedica, Inc., Bloomington, MN (US)

( * ) Notice: Subject to any disclaimer, the term of this patent is extended or adjusted under 35 U.S.C. 154(b) by 0 days.

(21) Appl. No.: 10/426,424

(22) Filed: Apr. 30, 2003

(65) Prior Publication Data

US 2004/0002764 A1    Jan. 1, 2004

Related U.S. Application Data

(63) Continuation-in-part of application No. 10/185,832, filed on Jun. 27, 2002, now abandoned.

(51) Int. Cl.
*A61F 2/44*    (2006.01)

(52) U.S. Cl. ............................ 623/17.11; 623/17.16; 606/213

(58) Field of Classification Search ............. 623/17.11, 623/17.13, 17.12, 17.16; 606/61, 213, 215

See application file for complete search history.

(56) References Cited

U.S. PATENT DOCUMENTS

| | | | | |
|---|---|---|---|---|
| 5,549,679 A | * | 8/1996 | Kuslich | 623/17.12 |
| 5,846,261 A | * | 12/1998 | Kotula et al. | 606/213 |
| 5,935,147 A | * | 8/1999 | Kensey et al. | 606/213 |
| 6,036,720 A | * | 3/2000 | Abrams et al. | 606/213 |
| 6,245,107 B1 | * | 6/2001 | Ferree | 606/61 |
| 2003/0181983 A1 | * | 9/2003 | Cauthen | 623/17.16 |
| 2004/0019381 A1 | * | 1/2004 | Pflueger | 623/17.11 |

FOREIGN PATENT DOCUMENTS

| | | |
|---|---|---|
| EP | 0 898 945 A1 | 8/1998 |
| WO | WO 01/21246 A1 | 3/2001 |
| WO | WO 01/28464 A1 | 4/2001 |
| WO | WO 01/56475 A1 | 8/2001 |

* cited by examiner

*Primary Examiner*—Bruce E. Snow
(74) *Attorney, Agent, or Firm*—Dicke, Billig & Czaja, PLLC

(57) ABSTRACT

An occlusion device for occluding a defect in a spinal disc anulus, including a plate and a retention device. The plate defines an anulus contact face. The retention device extends from the contact face of the plate and defines an anulus engagement portion. The retention device is deflectable relative to the plate such that in a deployed state, the retention device biases the plate against material disposed between the contact face of the plate and the anulus engagement portion. Upon final deployment, the retention device bears against the exterior surface of the anulus, biasing the plate into contact with the interior surface of the anulus. In a preferred embodiment, the retention device includes a pair of L-shaped arms each extending in an opposing, angular fashion from the plate.

13 Claims, 12 Drawing Sheets

US 7,033,393 B2

SELF-TRANSITIONING SPINAL DISC ANULUS OCCULSION DEVICE AND METHOD OF USE

CROSS-REFERENCE TO RELATED APPLICATIONS

This application is a continuation-in-part of U.S. application Ser. No. 10/185,832, filed Jun. 27, 2002 now abandoned, and entitled "Spinal Disc Anulus Occlusion Device and Method of Use".

BACKGROUND OF THE INVENTION

The present invention relates to a device for occluding a defect through a spinal disc anulus. More particularly, it relates to an occlusion device adapted to provide a strong mechanical closure or barrier for a spinal disc anulus defect.

The vertebral spine is the axis of the skeleton upon which all of the body parts "hang". In humans, the normal spine has seven cervical, twelve thoracic and five lumbar segments. The lumbar segments sit upon a sacrum, which then attaches to a pelvis, in turn supported by hip and leg bones. The bony vertebral bodies of the spine are separated by intervertebral discs, which act as joints, but allow known degrees of flexion, extension, lateral bending and axial rotation.

The typical vertebra has a thick interior bone mass called the vertebral body, and a neural (vertebral) arch that arises from a posterior surface of the vertebral body. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch that extends posteriorly and acts to protect a posterior side of the spinal cord is known as the lamina. Projecting from the posterior region of the neural arch is a spinous process. The central portions of adjacent vertebrae are separated and supported by an intervertebral disc.

The intervertebral disc primarily serves as a mechanical cushion between the vertebral bones, permitting controlled motions within vertebral segments of the axial skeleton. The normal disc is a unique, mixed structure, comprised of three component tissues: The nucleus pulposus ("nucleus"), the anulus fibrosus ("anulus"), and two opposing vertebral end plates. The two vertebral end plates are each composed of thin cartilage overlying a thin layer of hard, cortical bone which attaches to the spongy, richly vascular, cancellous bone of the vertebral body. The end plates thus serve to attach adjacent vertebrae to the disc. In other words, a transitional zone is created by the end plates between the malleable disc and the bony vertebrae.

The anulus of the disc is a tough, outer fibrous ring that binds together adjacent vertebrae. This fibrous portion, which is much like a laminated automobile tire, is generally about 10 to 15 millimeters in height and about 15 to 20 millimeters in thickness. The fibers of the anulus consist of 15 to 20 overlapping multiple plies, and are inserted into the superior and inferior vertebral bodies at roughly a 30 degree angle in both directions. This configuration particularly resists torsion, as about half of the angulated fibers will tighten when the vertebrae rotate in either direction, relative to each other. The laminated plies are less firmly attached to each other.

Immersed within the anulus, positioned much like the liquid core of a golf ball, is the nucleus. The anulus and opposing end plates maintain a relative position of the nucleus in what can be defined as a nucleus cavity. The healthy nucleus is largely a gel-like substance having high water content, and similar to air in a tire, serves to keep the anulus tight yet flexible. The nucleus-gel moves slightly within the anulus when force is exerted on the adjacent vertebrae with bending, lifting, etc.

Under certain circumstances, an anulus defect (or anulotomy) can arise that requires surgical attention. These anulus defects can be naturally occurring, surgically created, or both. A naturally occurring anulus defect is typically the result of trauma or a disease process, and may lead to a disc herniation. A disc herniation occurs when the anulus fibers are weakened or torn and the inner tissue of the nucleus becomes permanently bulged, distended, or extruded out of its normal, internal anular confines. The mass of a herniated or "slipped" nucleus can compress a spinal nerve, resulting in leg pain, loss of muscle control, or even paralysis.

Where the naturally occurring anulus defect is relatively minor and/or little or no nucleus tissue has escaped from the nucleus cavity, satisfactory healing of the anulus may be achieved by immobilizing the patient for an extended period of time. A more practical solution would be artificially obstructing or occluding the defect with an auxiliary device. Unfortunately, an effective anulus defect occluder able to maintain its position relative to an even minor anulus defect has not heretofore been developed.

A more problematic anulus defect concern arises in the realm of anulotomies encountered as part of a surgical procedure performed on the disc space. As a starting point, bed rest alone cannot adequately heal many disc herniations, such that a more traumatic surgical intervention is required. Alternatively, with discal degeneration, the nucleus loses its water binding ability and deflates, as though the air had been let out of a tire. Subsequently, the height of the nucleus decreases, causing the anulus to buckle in areas where the laminated plies are loosely bonded. As these overlapping laminated plies of the anulus begin to buckle and separate, either circumferential or radial anular tears may occur, which may contribute to persistent and disabling back pain. Adjacent, ancillary spinal facet joints will also be forced into an overriding position, which may create additional back pain.

In many cases, to alleviate pain from degenerated or herniated discs, the nucleus is removed and the two adjacent vertebrae surgically fused together. While this treatment alleviates the pain, all discal motion is lost in the fused segment. Ultimately, this procedure places greater stress on the discs adjacent the fused segment as they compensate for the lack of motion, perhaps leading to premature degeneration of those adjacent discs. A more desirable solution entails replacing, in part or as a whole, the damaged nucleus with a suitable prosthesis having the ability to complement the normal height and motion of the disc while stimulating the natural disc physiology.

The first prostheses embodied a wide variety of ideas, such as ball bearings, springs, metal spikes and other perceived aids. These prosthetic discs were designed to replace the entire intervertebral disc space, and were large and rigid. Beyond the questionable efficacy of these devices is the inherent difficulties encountered during implantation. Due to their size and inflexibility, these first generation devices require an anterior implantation approach as the barriers presented by the lamina and, more importantly, the spinal cord and nerve rootlets during posterior implantation, could not be avoided. Recently, smaller and more flexible prosthetic nucleus devices have been developed. With the reduction in prosthesis size, the ability to work around the spinal cord and nerve rootlets during posterior implantation has become possible.

Generally speaking, these reduced size prostheses are intended to serve as a replacement for the natural nucleus. In other words, the anulus and end plates remain intact, and the prosthesis is implanted within the nucleus cavity. In order to implant a prosthesis within the nucleus cavity, an appropriately sized passageway through the anulus (i.e., anulotomy) must exist. The requisite anulus defect can be surgically imparted as part of the surgical implantation procedure, or the naturally occurring anulus defect that caused or resulted from the discal failure may be large enough for passage of the prosthesis. One pre-implant anulotomy technique entails complete removal of a plug of tissue from the anulus via an incision created by a scalpel, punch or similar tool. Entire removal of an anulus segment is highly traumatic, and limits the ability of the anulus to properly heal. Attempts to reattach the anulus plug have been unavailing in that properly orienting and securing of the anulus plug with a suture has proven difficult at best. Alternatively, a flap can be imparted into the anulus tissue. This technique overcomes the reattachment problems associated with the anulus plug approach. Unfortunately, however, the thickness of the anulus requires formation of a relatively large flap, therefore increasing anulus trauma. Further, it may be difficult to retain the flap in a retracted position throughout the implantation procedure. A third, more viable procedure is to dilate a small opening or incision in the anulus to a size sufficient for prosthesis implantation. The overlapping, plied nature of the anulus tissue renders the anulus highly amenable to incision dilation.

Regardless of the anulotomy technique, the resulting anulus defect may lead to post-implant complications. The anulus tissue will, in theory, regenerate or naturally repair the defect over time. However, substantial scar tissue formation will not occur for a significant period of time, and requires that forces on the spinal tract be minimized (i.e., that the patient be immobilized). For virtually all patients, this is impossible to achieve. Instead, within several days of the implantation procedure, the patient must move about, thereby placing forces on the disc space. Because the anulus defect has not healed, it cannot readily prevent the prosthetic nucleus, or portions thereof (depending upon the particular prosthesis construction), from migrating back through the anulus defect. Even if this opening is closed via sutures following implant, various forces acting upon the disc space have the potential to overcome the resistance provided by the sutures and "push" the prosthesis back through the anulus opening. A more preferable solution would be the provision of an auxiliary device that serves to not only occlude the surgically-created anulus defect, but also rigidly resists explant of the prosthesis, or portions thereof, back through the opening. Unfortunately, and as previously described, such a device has not heretofore been developed.

Spinal disc anulus defects occur both naturally and as part of a surgical procedure. Currently accepted techniques of suturing the defect closed are of minimal value in light of the forces normally encountered by the disc space. Even more problematic is the inability to protect against explant of a prosthetic spinal disc nucleus otherwise implanted through a surgical-imparted anulus defect. Therefore, a need exists for a spinal anulus defect occlusion device capable of effectuating anulus repair and providing a strong mechanical closure/barrier required for successful prosthetic disc nucleus implantation.

SUMMARY OF THE INVENTION

One aspect of the present invention relates to an occlusion device for occluding a defect in a spinal disc anulus. The spinal disc anulus has an interior surface and an exterior surface, and defines an internal cavity. With this in mind, the occlusion device includes a plate and a retention device. The plate defines an anulus contact or inner face, and is configured for deployment within the internal cavity. The retention device extends from the contact face of the plate and defines an anulus engagement portion. In this regard, the retention device is deflectable relative to the plate such that in a deployed state, the retention device biases the plate against material disposed between the contact face of the plate and the anulus engagement portion. With this construction, the occlusion device is configured such that upon final deployment, the retention device bears against the exterior surface of the anulus, biasing the plate into contact with the interior surface of the anulus. In a preferred embodiment, the retention device includes a pair of L-shaped arms each extending in an opposing, angular fashion from the plate. The so-defined arms are rigid yet deflectable, able to compensate for variations in a thickness of the anulus.

Another aspect of the present invention relates to a method of occluding a defect in a spinal disc anulus. Once again, the anulus includes an exterior surface and an interior surface, and defines an internal cavity. With this in mind, the method includes providing an occlusion device including a plate and a retention component extending from an anulus contact face of the plate and terminating in an anulus engagement portion. The plate is deployed within the internal cavity defined by the spinal disc anulus such that the contact face thereof faces the interior surface in a region of the defect. The retention component is deployed such that the anulus engagement portion contacts the exterior surface of the anulus adjacent the defect. Upon final deployment, the retention component biases the plate into engagement with the anulus, thereby securing the occlusion device to the anulus. In one preferred embodiment, the retention component is collapsible relative to the plate, with the method further comprising collapsing the occlusion device to the insertion state prior to the step of deploying the plate within the internal cavity.

Yet another aspect of the present invention relates to a method of implanting a prosthetic spinal disc nucleus into a nucleus cavity defined by an anulus. In this regard, the anulus defines an interior surface and an exterior surface. With this in mind, the method includes creating an opening through the anulus. A prosthetic spinal disc nucleus is inserted into the nucleus cavity through the opening. An occlusion device is provided that includes a plate and a retention component extending from an anulus contact face of the plate and terminating in an anulus engagement portion. The plate is deployed within the internal cavity via the opening. The retention component is deployed such that the anulus engagement portion contacts the exterior surface of the anulus adjacent the defect. Upon final deployment, the retention component biases the plate into engagement with the anulus, thereby securing the occlusion device to the anulus. The so-secured occlusion device rigidly resists expulsion of the prosthetic spinal disc nucleus back through the opening.

DESCRIPTION OF THE PREFERRED EMBODIMENTS

Figure 1:
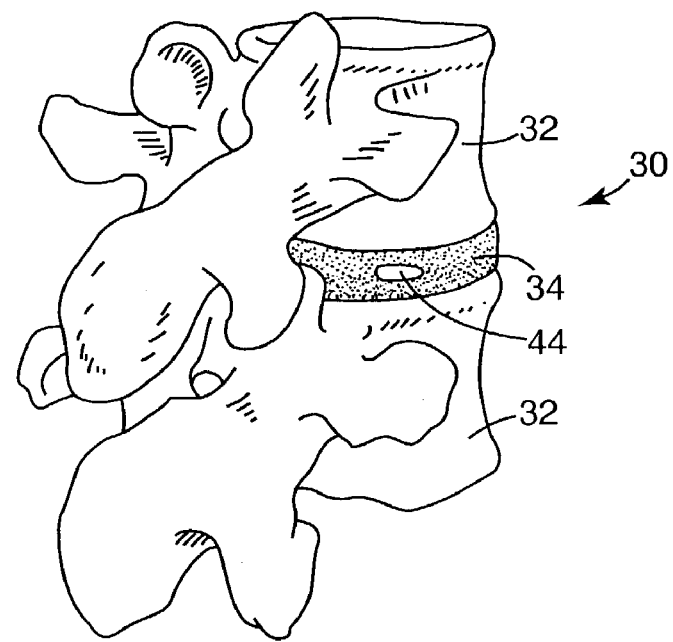
FIG. 1 is a posterior view of a spinal segment including a discal area within the which the device and method of the present invention are useful.
Figure 2:
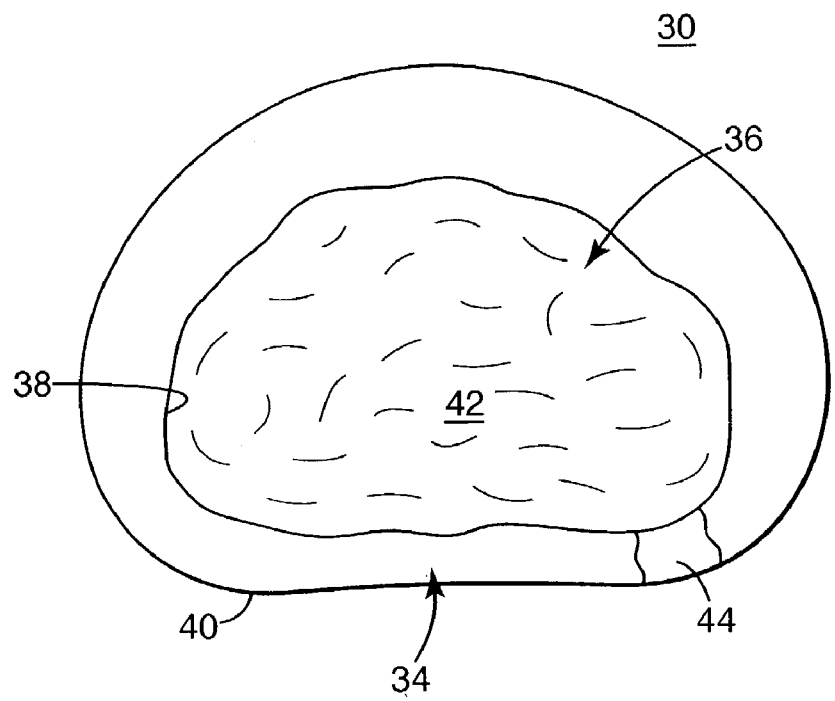
FIG. 2 is an enlarged top, sectional view of the disc space of FIG. 1.

The present inventions relates to an occlusion device for occluding a defect in a spinal disc anulus. As a point of reference, FIGS. 1 and 2 depict a disc space 30 for which the device and method of the present invention are applicable. The disc space 30 separates adjacent vertebrae 32 and includes an anulus 34 and a nucleus 36 (shown in FIG. 2). The anulus 34 defines an inner surface 38 and an outer surface 40. Further, the anulus 34, in combination with end plates (not shown) associated with the opposing vertebrae 32, defines a nucleus cavity 42 (referenced generally in FIG. 2) within which the nucleus 36 is contained. With the illustrations of FIGS. 1 and 2, a defect 44 is formed in the anulus 34. The defect 44 can be naturally occurring, such as a tear or other trauma to the anulus 34. Alternatively, or in addition, the defect 44 can be surgically created as part of a disc space repair procedure. For example, and as described in greater detail below, a small incision may be formed in the anulus 34 to facilitate implantation of a prosthesis (not shown) into the nucleus cavity 42. Thus, although the defect 44 is illustrated in FIGS. 1 and 2 as being relatively uniform, the defect 44 can assume a wide variety of shapes and sizes.

Figure 3:
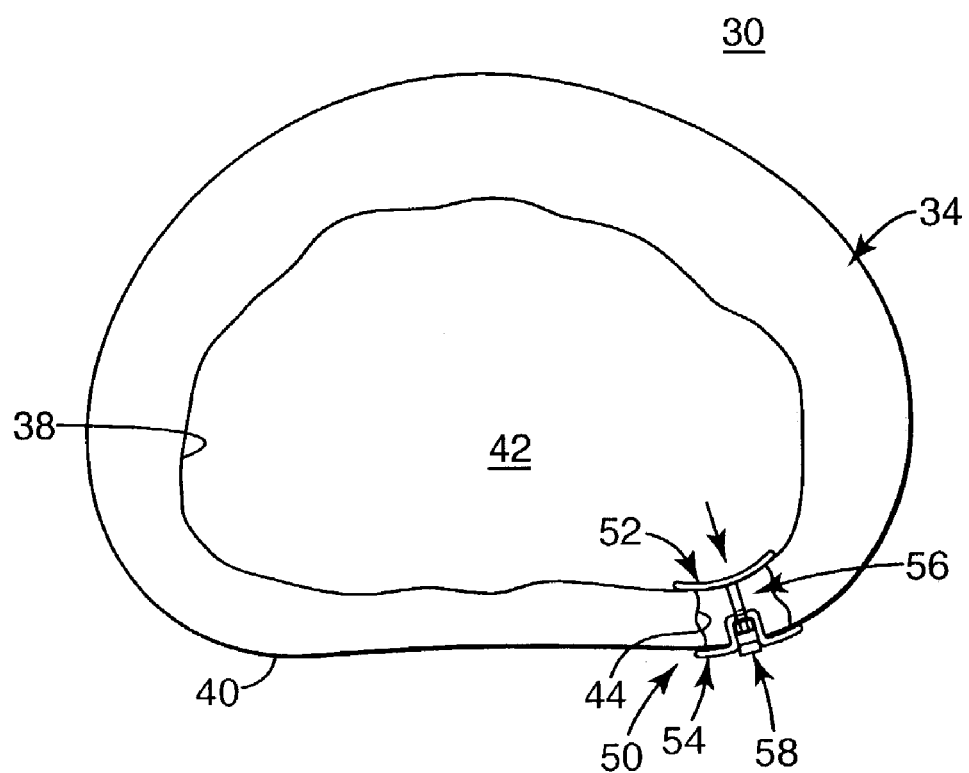
FIG. 3 is a top, sectional view of the disc space of FIG. 2 in conjunction with a deployed occlusion device in accordance with the present invention.

With the above definitions in mind, FIG. 3 illustrates one preferred embodiment of an occlusion device 50 in accordance with the present invention deployed to the above-described disc space 30. For ease of illustration, the nucleus 36 has been removed from the view of FIG. 3. With this in mind, the occlusion device 50 is configured to satisfy the unique constraints presented by the disc space 30, and includes a first member 52, a second member 54, a connector 56, and a cap 58. The various components are described in greater detail below. In general terms, however, the first member 52 is secured to the second member 54 by the connector 56. Upon final deployment, the first member 52 engages the inner surface 38 of the anulus 34. Similarly, the second member 54 engages the outer surface 40 of the anulus 34. The connector 56 extends through the defect 44 and rigidly secures the first and second members 52, 54 to the anulus 34. Finally, the cap 58 is secured to the second member 54, and covers the connector 56 relative to an exterior of the anulus 34. Rigid engagement of the occlusion device 50 relative to the anulus 34 serves to prevent transverse displacement or movement of the first member 52 outwardly through the defect 44.

Figure 4:
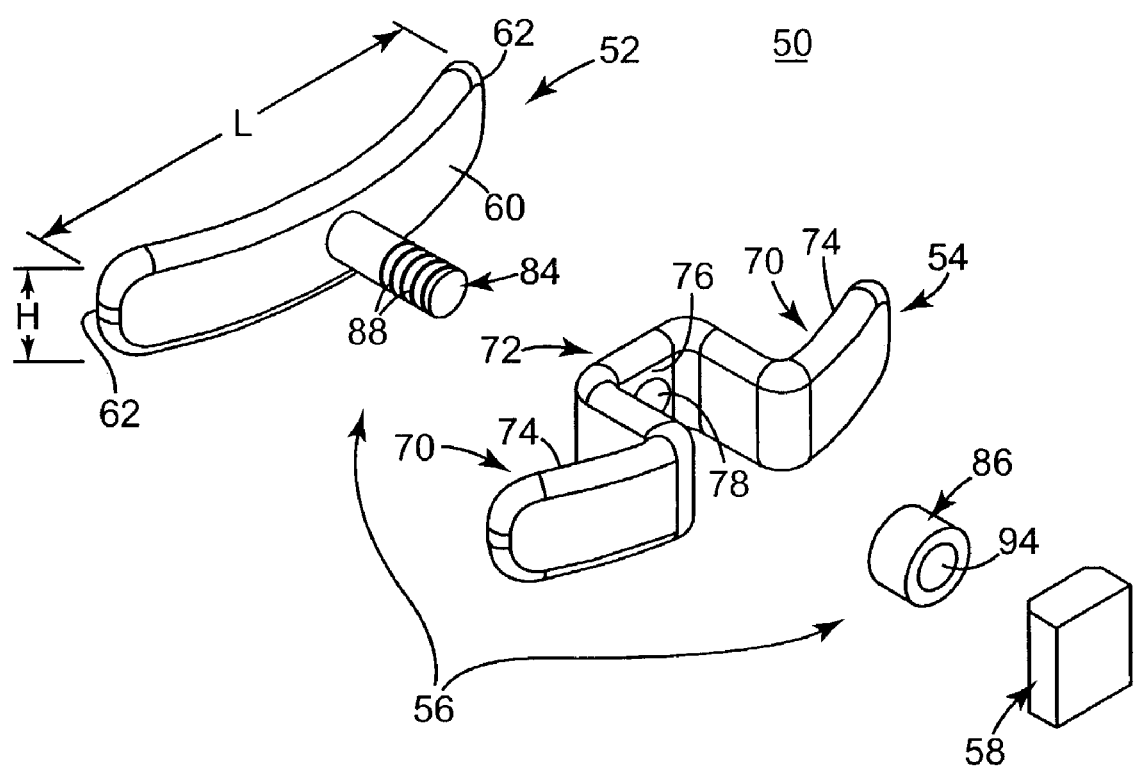
FIG. 4 is an exploded, perspective view of the occlusion device of FIG. 3.

With additional reference to FIG. 4, the first member 52 is preferably in the form of a rigid, elongated plate that defines an anulus contact face 60 extending between opposing ends 62. The anulus contact face 60 is generally convex, conforming with a general shape of the inner surface 38 of the anulus 34. A length ("L" in FIG. 4) of the first member 52 can vary depending upon the particular application (e.g., generally longer for use in maintaining a previously-implanted prosthetic disc nucleus as compared to general anulotomy repair), but is preferably on the order of 10–30 mm in length. It has surprisingly been found that providing the first member 52 with a length in the range of 10–30 mm facilitates relatively easy insertion into the nucleus cavity 42 while providing sufficient surface area for encompassing most normally encountered anulus defects and anulus engagement as described below. Further, the first member 52 has a height ("H" in FIG. 4) that approximates an expected height of the anulus 34. In a preferred embodiment, the first member 52 has a height on the order of 5–15 mm. Although not illustrated in FIG. 4, in one alternative embodiment, the opposing ends 62 are preferably relatively sharp to assist in engaging or "biting" into the anulus 34 upon final deployment. Finally, the first member 52 is preferably formed from a strong, biocompatible material, including metals or plastics, such as polyetheretherketone (PEEK), carbon fiber composite, etc. These preferred dimensions and materials have surprisingly been found to facilitate transversely rigid engagement between the first member 52 and the anulus 34 as described below.

The second member 54 is preferably formed as an elongated, rigid body. In this regard, the second member 54 includes opposing outer regions 70 and a central region 72. The opposing outer regions 70 combine to define an anulus contact face 74 that, in a preferred embodiment, is generally concave, thereby conforming generally with the shape of the outer surface 40 of the anulus 34. The central region 72 projects distally relative to the opposing outer regions 70, thereby defining an indentation. In other words, the second member 54 includes an outer face 76 that forms the indentation at the central region 72 relative to the opposing outer regions 70. As described in greater detail below, the central region 72 is preferably sized to project within the defect 44 upon deployment of the second member 54 to the outer surface 40 of the anulus 34, providing a self-centering feature and preventing movement of the device 50 following deployment. Finally, the central region 72 includes a passage 78 sized to receive a portion of the connector 56 as described below.

Similar to the first member 52, the second member 54 is preferably formed of a relatively rigid, biocompatible material such as PEEK, carbon fiber composite, etc. Further, the second member 54 preferably has height and width (or length) dimensions similar to those of the first member 52. Alternatively, however, and because the second member 54 is not deployed within the nucleus cavity 42, the second member 54 can be slightly larger than the first member 52.

The connector 56 preferably includes a post 84 and a coupler 86. The post 84 extends proximally from the anulus contact face 60 of the first member 52. In this regard, the post 84 is preferably centered relative to a length of the first member 52. Further, the post 84 is sized to be slidably received within the passage 78 of the second member 54, and preferably forms a series of notches 88. As described below, the notches 88 facilitate locking engagement between the post 84 and the coupler 86. As such, other coupling designs, such as threads, can be employed. Regardless, the post 84 is preferably formed of a relatively rigid, biocompatible material such as PEEK, carbon fiber composite, etc., and defines a length (or extension from the anulus contact face 60) commensurate with an expected transverse width of the anulus 34. Thus, in one preferred embodiment, the post 84 has a length in the range of approximately 5–15 mm.

The coupler 86 is a ring-like component, and defines a central hole 94 sized to slidably receive the post 84. Further, the coupler 86 preferably defines one or more internal, deflectable fingers (not shown) that extend radially within the central hole 94. The fingers are configured to selectively engage each of the notches 88 as the coupler 86 is forced along the post 84. More particularly, the fingers facilitate locking of the coupler 86 relative to the post 84 as the fingers engage a respective one of the notches 88. That is to say, in a preferred embodiment, the fingers allow the coupler 86 to be slid distally along the post 84, but prevent proximal (or rearward) movement of the coupler 86 relative to the post 84 once the fingers have engaged a particular one of the notches 88, such that the coupler 86 serves as a locking component. Alternatively, a wide variety of other locking techniques, such as threads, can be employed.

Finally, the cap 58 is configured to selectively engage the second member 54 at the central region 72. For example, the outer face 76 of the central region 72 can form grooves sized to frictionally receive opposing edges of the cap 58 in a snap-fit relationship. Alternatively, the cap 58 and/or the second member 54 can incorporate other configurations that facilitate assembly of the cap 58 to the second member 54. Regardless, the cap 58 serves to cover the indentation otherwise defined by the central region 72 upon final deployment, and is preferably configured to mesh with a profile of the second member 54.

Figure 5A:
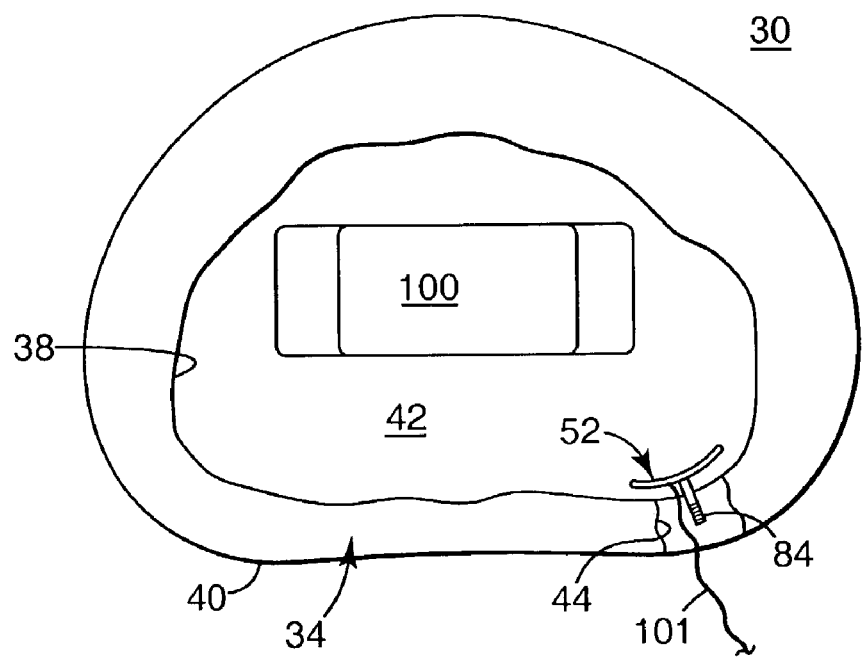
FIGS. 5A–5C illustrate a method of deploying the occlusion device of FIG. 4.
Figure 5B:
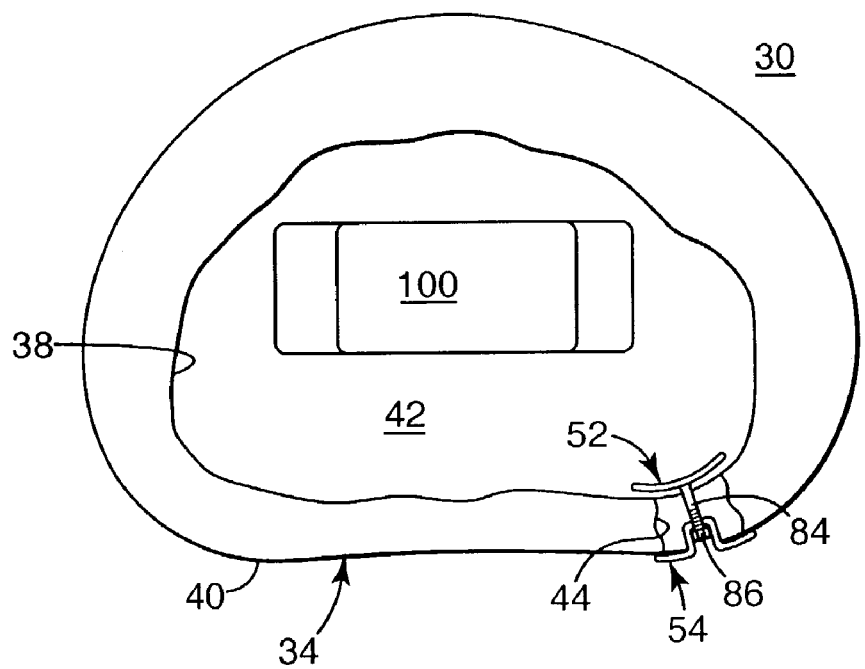
Figure 5C:
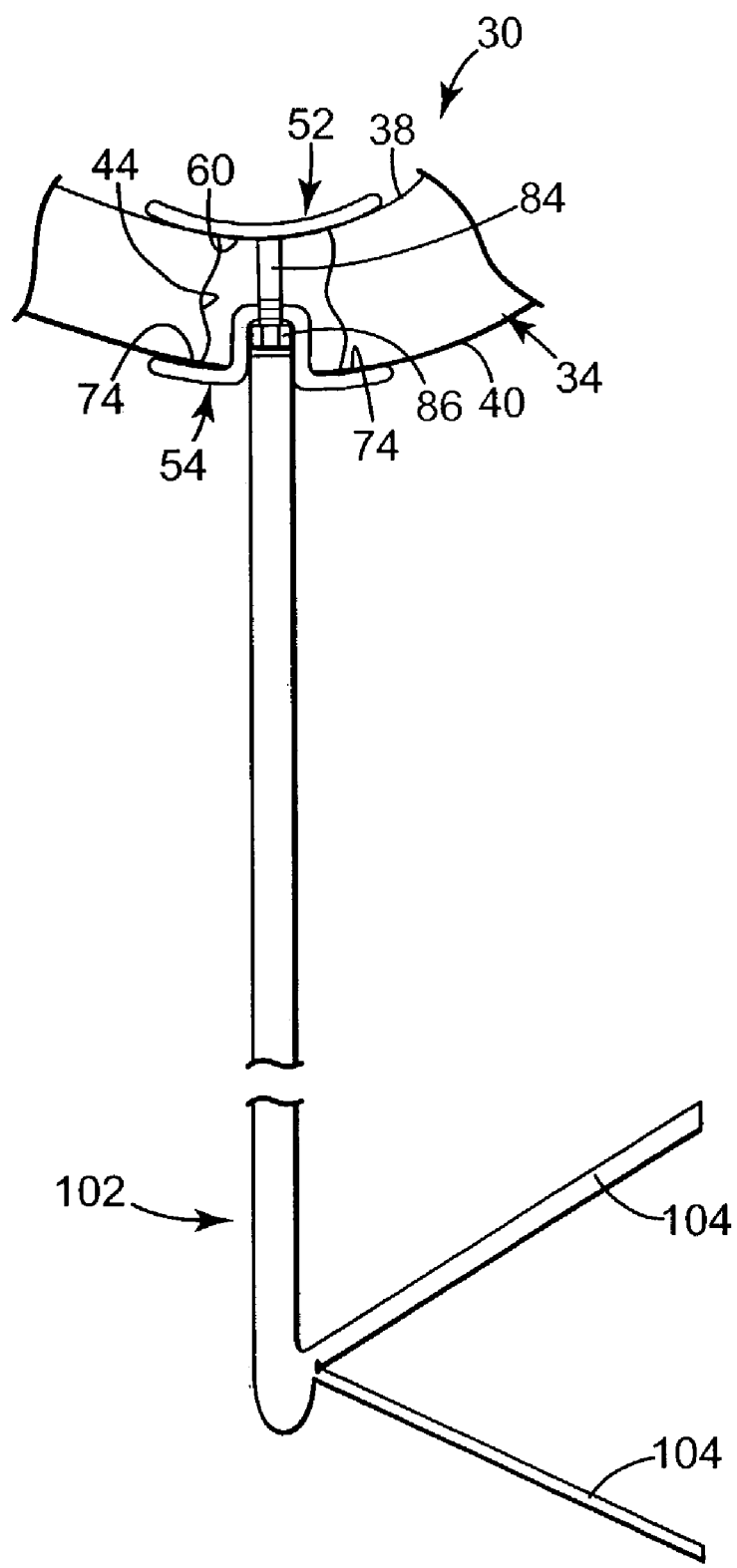

Deployment of the occlusion device 50 to a disc space 30 is best described with reference to FIGS. 5A–5C. As a point of reference, the deployment methodology associated with FIGS. 5A–5C is provided in conjunction with a prosthetic spinal disc nucleus implantation procedure. In particular, the defect or passage 44 is imparted through the anulus 34. In one preferred embodiment, some or all of the nucleus material 36 (FIG. 1) is removed from the nucleus cavity 42. A prosthetic spinal disc nucleus 100 (shown generally in FIGS. 5A and 5B) is then implanted into the nucleus cavity 42 as shown in FIG. 5A. It will be understood that the prosthetic nucleus 100 illustrated in FIGS. 5A and 5B is but one example of an acceptable device and is in no way limiting; a prosthetic nucleus can have a wide variety of shapes, sizes, materials, constructions, etc., as is known in the art.

Following implantation of the prosthetic spinal disc nucleus 100, the first member 52 is inserted through the defect 44 and positioned within the nucleus cavity 42 as shown. To facilitate handling and temporary retention of the first member 52 during this insertion or deployment operation, a suture 101 or other removable component can be connected to the first member 52 and extended outwardly from the nucleus cavity 42 via the defect 44. Alternatively, the post 84 provides a convenient surface for handling the first member 52 during the deployment procedure, such that the suture 101 or other removable component is not required.

With the first member 52 properly positioned, the second member 54 is then deployed relative to the outer surface 40 of the anulus 34 as shown in FIG. 5B. In particular, the second member 54 is positioned such that the post 84 extends through the passage 78 (FIG. 4) of the second member 54. The coupler 86 is then placed over the post 84 as shown. Notably, in FIG. 5B, the spacing between the first and second members 52, 54 is such that the first and second members 52, 54 do not intimately engage or contact the respective inner and outer surfaces 38, 40 of the anulus 34. Instead, the first and second members 52, 54 are "loose" relative to the anulus 34. Where provided, the suture 101 (FIG. 5A) or other component is removed.

The first and second members 52, 54 are then drawn toward one another by forcing the coupler 86 distally along the post 84. In this regard, a clamping tool 102 (shown generally in FIG. 5C) can be provided that mechanically engages the coupler 86 and the post 84, and drives the coupler 86 along the post 84 via movement of handle grips 104. Alternatively, the surgeon can employ other tools and/or manually force the coupler 86 along the post 84. Regardless, the coupler 86 locks (i.e., cannot proximally retract relative to the post 84) at each successively engaged notch 88 (FIG. 4). As the first and second members 52, 54 are forced toward one another, the respective anulus contact faces 60, 74 engage the inner and outer surfaces 38, 40 of the anulus 34. In other words, the anulus 34 is sandwiched between the first and second members 52, 54, and is pinched therebetween. This pinching or compressive force secures the first and second members 52, 54 relative to the anulus 34 in the region of the defect 44. Once desired engagement between the first and second members 52, 54 and the anulus 34 has been achieved, the cap 58 is secured to the second member 54 as shown in FIG. 3.

By preferably configuring the occlusion device 50, and in particular the connector 56, such that a spacing between the first and second members 52, 54 is adjustable, the occlusion device 50 can be used with a variety of different thickness anuli. Further, due to the relatively rigid construction of the first and second members 52, 54, as well as the relatively rigid engagement with the anulus 34, the occlusion device 50 resists undesirable migration or explant of the first member 52 back through the defect 44. In this regard, it should be understood that following the deployment procedure, the disc space 30 will be subjected to normal loads. In response to these loads, the disc space 30 imparts a pushing force on the first member 52 (i.e., transverse force relative to a length of the first member 52, indicated by an arrow in FIG. 3). Construction of the occlusion device 50 in conjunction with pinched engagement of the first and second members 52, 54 to the anulus 34 prevents this pushing force from ejecting the first member 52 back through the defect 44.

When employed as part of a prosthetic spinal disc nucleus implantation procedure, the occlusion device 50 provides the further advantage of resisting not only displacement of the occlusion device 50 itself, but also of the previously-implanted prosthetic spinal disc nucleus 100. In this regard, the normal loads placed on the disc space 30 may cause the prosthetic spinal disc nucleus 100 to migrate from the position shown in FIGS. 5A–5C back toward the defect 44 through which the prosthetic spinal disc nucleus 100 was initially implanted. Alternatively, the prosthetic spinal disc nucleus 100 can have an entirely different construction (e.g., sized to encompass an entirety of the nucleus cavity 42, highly amorphous, etc.), such that a portion of the prosthesis 100 readily contacts the first member 52 following implant and deployment. Regardless, the occlusion device 50 prevents explant or extrusion of the prosthetic spinal disc nucleus 100 or a portion thereof by not only occluding the defect 44, but also by providing strong structural support in the region of the defect 44 such that the occlusion device 50 resists a transverse force otherwise generated by the prosthetic spinal disc nucleus 100 directly on the first member 52. As a point of reference, occlusion devices for occluding cardiac septal defects are known. However, these cardiac septal occluders are configured for the sole purpose of blocking liquid flow, and provide virtually no transverse force resistance. Thus, septal defect occluders have no usefulness for spinal disc anulus repair. The transverse force resistance provided by the occlusion device 50 of the present invention is at least 10 times, more preferably at least 100 times, that provided by known septal defect occluders. Thus, for example, upon final deployment, the occlusion device 50 of the present invention provides transverse force resistance of at least 10 lbs.-force.

As described in greater detail below, the occlusion device in accordance with the present invention can assume configurations varying from the occlusion device 50 associated with the one preferred embodiment. As a general statement, however, components of the occlusion device 50 can incorporate additional features that facilitate repair of the anulus 34. For example, the first and/or second members 52, 54 can be configured to promote tissue regeneration by incorporating a scaffolding construction that can deliver tissue in-growth promoting materials. Alternatively, the first and/or second members 52, 54 can include perforations that promote anulus tissue in-growth. Further, the first and/or second members 52, 54 can provide a roughened/machined surface (e.g., the anulus contact face(s) 60, 74) to assist in maintaining a desired positioning upon final deployment. Also, the occlusion device 50, or components thereof, can be coated, treated, or formed in such a way as to reduce fibrosis or other tissue formation, especially at the outer face 76 of the second member 54 that is otherwise closest to the dura (not shown) of the spinal cord or other nerve tissue. Conversely, one or both of the anulus contact surfaces 60, 74 can be coated or treated in such a way as to induce tissue in-growth for attachment purposes and/or for anulus healing (e.g., scar formation).

Figure 6A:
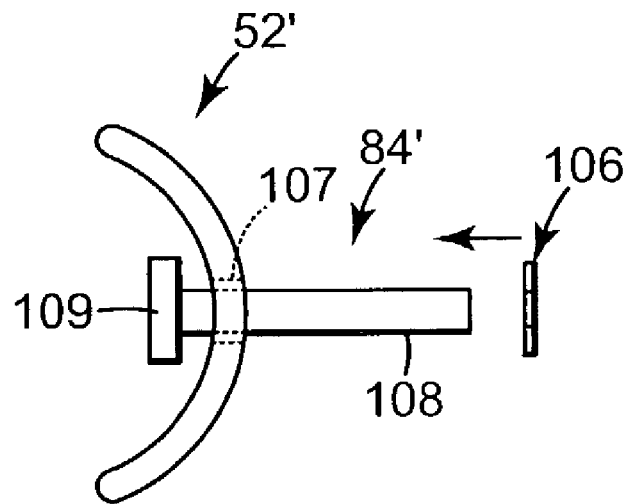
FIGS. 6A and 6B are a side view of alternative embodiment components of the device of FIG. 4.

In one alternative embodiment, the first member 52 and the post 84 are provided as separate components to facilitate ease of insertion through the defect or passage 44. For example, FIG. 6A depicts an alternative first member 52' and an alternative post 84' in conjunction with a tightening member 106 in a partially assembled state. The first member 52' is highly similar to that previously described, but is formed of a more flexible material that is biased to a normally folded shape (shown in FIG. 6A) and defines an aperture 107. The post 84' includes a shaft 108 sized to be received through the aperture 107 and an enlarged base 109. Finally, the tightening member 106 is configured to be received over the shaft 108, and lock thereon. For example, in one preferred embodiment, the tightening member 106 is a speed nut.

Figure 6B:
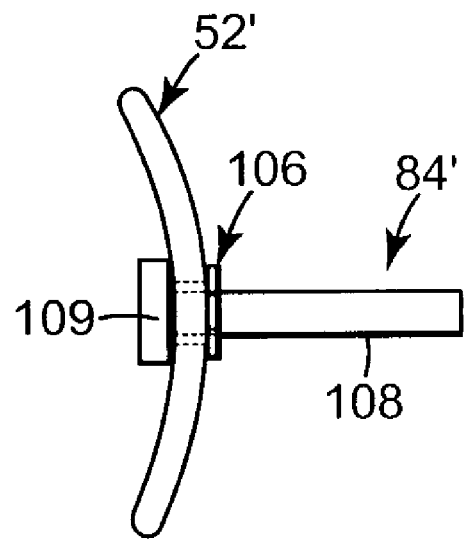

Prior to final assembly, the shaft 108 is placed through the aperture 107 and the tightening member 106 is connected thereto as shown in FIG. 6A. However, the base 109 is "loose" relative to the first member 52' such that the first member 52' assumes the naturally folded or compressed shape. As such, the first member 52' is more easily inserted through the annulus defect or passage 44 (FIG. 5A). Once inserted, the tightening member 106 is forced toward the first member 52', causing the base 109 to press inwardly against the first member 52'. This action, in turn, causes the first member 52' to unfold or straighten to the deployed position illustrated in FIG. 6B.

Figure 7:
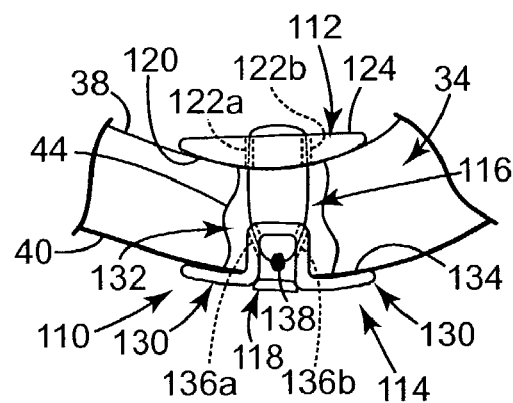
FIG. 7 is a top, sectional view of a portion of the disc space of FIG. 2 in conjunction with a deployed, alternative embodiment occlusion device in accordance with the present invention.

An alternative embodiment occlusion device 110 is provided in FIG. 7, and is illustrated as deployed relative to the anulus 34. The occlusion device 110 is highly similar to the occlusion device 50 previously described, and includes a first member 112, a second member 114, a connector 116, and a cap 118. In general terms, the occlusion device 110 is deployed in a manner similar to that previously described, with the first member 112 engaging the inner surface 38 of the annulus 34, and the second member 114 engaging the outer surface 40 of the anulus 34. The connector 116 connects the first and second members 112, 114, and facilitates forcing the first and second members 112, 114 to the position shown in FIG. 7, as well as securing the components in that position. Finally, the cap 118 is preferably provided to enclose a relevant portion of the connector 116.

The first member 112 is virtually identical to the first member 52 (FIG. 4) previously described, and defines an anulus contact face 120. The first member 112 further forms two passages 122a, 122b that are sized to slidably receive a corresponding portion of the connector 116. In this regard, the passages 122a, 122b preferably extend through an entire thickness of the first member 112 (i.e., the passages 122a, 122b are open at both the anulus contact face 120 and a rear face 124), and are preferably centered relative to a length of the first member 112.

The second member 114 is likewise preferably highly similar to the second member 54 (FIG. 4) previously described, and includes opposing outer regions 130 and a central region 132. The opposing outer regions 130 combine to define an anulus contact face 134. The central region 132 projects distally relative to the opposing outer regions 130, thereby defining an indentation. The second member 114 further forms two passages 136a, 136b in the central region 132. The passages 136a, 136b are positioned to be aligned with the passages 122a, 122b, respectively, of the first member 112 upon final deployment, and are sized to slidably receive a portion of the connector 116.

The connector 116 is a thin, flexible thread (e.g., suture, wire, cable, etc.) that is sized to be sidably received within the passages 122a, 122b, 136a, 136b. Prior to deployment about the anulus 34, the connector thread 116 is threaded through the first passage 136a of the second member 114, through the first passage 122a of the first member 112, around or behind the first member 112, back through the second passage 122b of the first member 112, and finally back through the second passage 136b of the second member 114. To best show this one preferred threading arrangement, the connector thread 116 is illustrated in FIG. 7 as being spaced from an outer face 124 of the first member 112. In practice, however, the connector thread 116 will be tight about the first member 112 upon final deployment.

The above-described arrangement provides for sliding engagement between the connector thread 116 and the first and second members 112, 114. Thus, the connector thread 116 facilitates sliding movement of the second member 114 relative to the first member 112. During use, then, with the first and second members 112, 114 threaded to the connector 116, the second member 114 is retracted relative to the first member 112. The first member 112 is inserted through the defect 44 and into the nucleus cavity 42 (FIG. 5A). The connector thread 116 is available to approximately center the first member 112 relative to the defect 44. The second member 114 is then slid along the connector thread 116 to the final, deployed position illustrated in FIG. 7. In this regard, the surgeon preferably grasps opposing ends of the connector thread 116 proximal the second member 114 to facilitate achieving a tight compression of the first and second members 112, 114 about the anulus 34. Once properly positioned (e.g., the anulus contact face 120 of the first member 112 engaging the inner surface 38 of the anulus 34, and the anulus contact face 134 engaging the outer surface 40 of the anulus 34), a knot 138 is formed in the connector thread 116, thereby securing the occlusion device 110 to the position shown in FIG. 7. Finally, the cap 118 is secured to the second member 114 as previously described. Notably, by preferably extending the connector thread 116 around the first member 112 (i.e., along the rear face 124), the above-described tightening action more easily directs the first member 112 into desired engagement with the inner surface 38 of the anulus 34.

Figure 8A:
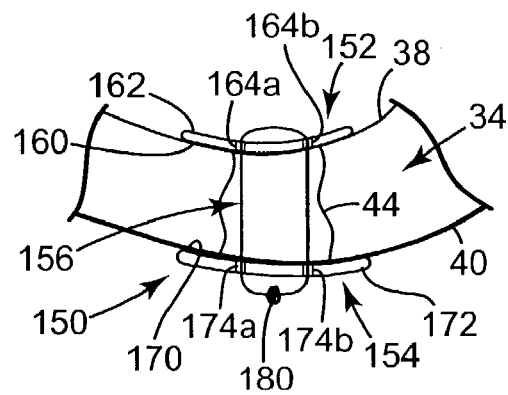
FIG. 8A is a top, sectional view of a portion of the disc space of FIG. 2 in conjunction with a deployed, alternative embodiment occlusion device in accordance with the present invention.
Figure 8B:
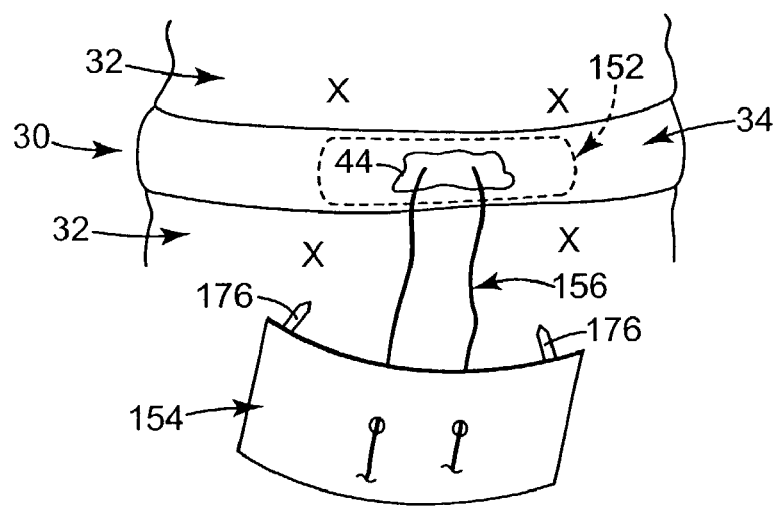
FIG. 8B is a posterior view of a spinal segment and illustrates deployment of the occlusion device of FIG. 8A.

Yet another alternative embodiment occlusion device 150 is shown in FIGS. 8A and 8B in conjunction with the disc space 30 previously described. Once again, the occlusion device 150 includes a first member 152, a second member 154, and a connector 156. As with previous embodiments, the connector 156 rigidly secures the first and second members 152, 154 about the anulus 34 upon final deployment.

The first member 152 is preferably an elongated plate defining an anulus contact face 160, a rear face 162, and passages 164a, 164b. As with previous embodiments, the anulus contact face 160 is preferably generally convex. Further, the first member 152 is sized in accordance with the dimensions previously ascribed for the first member 52 (FIG. 4).

The second member 154 similarly defines an anulus contact face 170, an outer face 172, and passages 174a, 174b. Unlike previous embodiments, the anulus contact face 170 of the second member 154 is substantially continuous (i.e., does not form an indentation), but is generally concave in shape. With additional reference to FIG. 8B, the second member 154 preferably has a height that is greater than an expected height of the anulus 34, and forms distally extending pins 176 at the outer edges thereof. As a point of reference, the view of FIG. 8B illustrates two of the pins 176 disposed adjacent upper corners of the second member 154. It will be understood that in a preferred embodiment, two additional pins disposed adjacent lower corners of the second member 154. With this one preferred embodiment, the pins 176 are configured to anchor the second member 154 into the opposing vertebrae 32. FIG. 8B illustrates the expected contact points between the pins 176 and the opposing vertebrae 32 with an "x".

Finally, similar to the occlusion device 110 (FIG. 7) previously described, the connector 156 is preferably a thread (e.g., suture) that is slidably received within the various passages 164a, 164b, 174a, 174b. Once again, this preferred configuration allows the first and second members 152, 154 to slide along the connector 156, such that a deployed spacing between the members 152, 154 is adjustable.

During use, following threading of the connector thread 156 to the first and second members 152, 154, the first member 152 is inserted into the nucleus cavity 42 (best shown in FIG. 5A) via the defect 44. The first member 152 is then approximately positioned to the orientation shown in FIG. 8A. The second member 154 is then slid along the connector 156 as shown in FIG. 8B. In particular, the second member 154 is positioned such that the pins 176 contact the adjacent vertebrae 32. The pins 176 are then lodged into the adjacent vertebrae 32, thereby anchoring the second member 154 relative to the disc space 30. Opposing sides 178a, 178b of the connector thread 156 are then simultaneously pulled, drawing the first member 152 toward the second member 154. In particular, the anulus contact face 160 of the first member 152 is directed into engagement with the inner surface 38 of the anulus 34. Once a desired spacing between the first and second members 152, 154 has been achieved (i.e., the anulus 34 being sufficiently pinched between the first and second members 152, 154), a knot 180 is formed in the connector thread 156, thereby securing the occlusion device 150. Notably, while the occlusion device 150 has been described as forming the second member 154 to preferably include the anchor pins 176, these components can be eliminated such that the second member 154 is not mechanically fastened to the adjacent vertebrae 32.

Figure 9A:
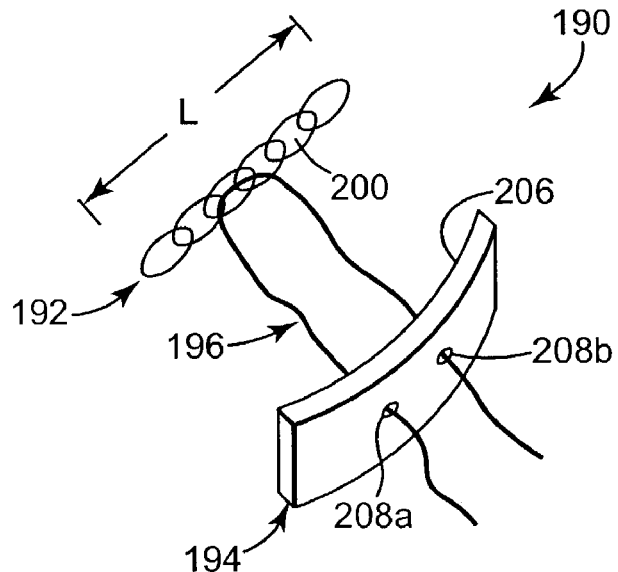
FIG. 9A is a perspective view of an alternative embodiment occlusion device in accordance with the present invention upon final deployment.
Figure 9B:
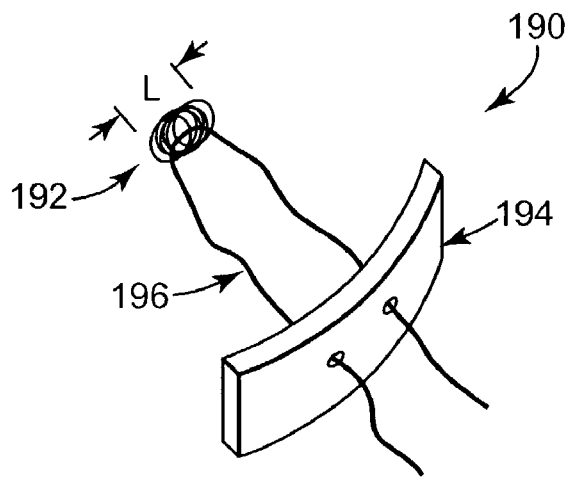
FIG. 9B illustrates the occlusion device of FIG. 9A in a delivery state.

Yet another alternative embodiment occlusion device 190 is provided in FIGS. 9A and 9B. As a point of reference, the occlusion device 190 is shown in FIG. 9A in a final, deployed position, whereas FIG. 9B depicts the occlusion device 190 in a delivery state. With this in mind, the occlusion device 190 includes a first member 192, a second member 194, and a connector 196. In general terms, the first member 192 is configured to be self-expandable from the delivery state (FIG. 9B) to the deployed state (FIG. 9A). The second member 194 is preferably similar to previous embodiments, as is the connector 196. With this general configuration, then, the connector 196 secures the first and second members 192, 194 about the anulus 34 (FIG. 2) upon final deployment.

The first member 192 is preferably a coiled wire (e.g., stainless steel or metal alloy having a shape memory characteristic such as NiTi) that can be longitudinally retracted (i.e., coiled upon itself to provide a reduced overall length "L" in FIGS. 9A and 9B). In the deployed position of FIG. 9A, the first member 192 defines an anulus contact face 200 (referenced generally). In this regard, the first member 192 is preferably configured such that in the deployed state, the first member 192 is relatively transversely rigid. However, the anulus contact face 200 is shaped in accordance with a contour of the individual coils, and is thus not necessarily convex. Alternatively, the first member 192 can assume other forms capable of providing a self-expanding characteristic such that the first member 192 can be contracted to a reduced length prior to deployment. For example, the first member 192 can be a flexible plate that is foldable on to itself (e.g., formed of polyethylene) or as a hydrogel-based component that expands in a predetermined fashion upon imbibing water.

The second member 194 is preferably similar to previous embodiments and defines an anulus contact face 206 and passages 208a, 208b. Thus, the second member 194 is preferably an elongated, relatively rigid plate. Alternatively, the second member 194 can assume the expandable, coil configuration previously described with respect to the first member 192. Finally, similar to previous embodiments, the connector 196 is preferably a flexible thread (e.g., suture) that extends through the passages 208a, 208b, as well as about one or more of the coils provided by the first member 192. Once again, this configuration provides a sliding relationship of the second member 194 relative to the first member 192 along the connector thread 196.

During use, the connector thread 196 is slidably secured to one or more of the coils provided by the first member 192. The first member 192 is then retracted to the delivery state shown in FIG. 9B. With this reduced profile, the first member 192 can be placed within a cannula (not shown) that maintains the first member 192 in the retracted position. The cannula is then inserted through the defect 44 (FIG. 2) such that a distal end thereof is positioned within the nucleus cavity 42. The first member 192 is then released from the cannula and into the nucleus cavity 42. Once released, the first member 192 self-expands from the delivery state of FIG. 9B to the deployed state of FIG. 9A. The connector thread 196 is then slidably connected to the second member 194 via the passages 208a, 208b. Finally, the second member 194 is forced toward the first member 192, and the connector thread 196 secured, as previously described (e.g., a knot is formed). In another alternative embodiment, the preferred configuration of the first and second members (192, 194) are reversed, such that the first member 192 is a relatively rigid plate and the second member 194 has a self-expanding construction.

Figure 10:
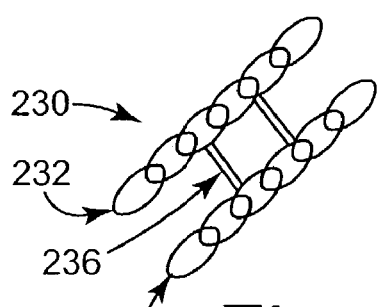
FIG. 10 is a perspective view of an alternative embodiment occlusion device in accordance with the present invention.

While previous embodiments have described the occlusion device as including separately formed first member, second member, and connector components, a unitary structure can alternatively be provided. For example, FIG. 10 illustrates an alternative embodiment occlusion device 230 that includes a first member 232, a second member 234, and a connector 236. The first and second members 232, 234 are preferably similar to the first member 192 (FIGS. 9A and 9B) previously described, and are each configured to be self-expanding from a delivery state (not shown) to a deployed state shown in FIG. 10. Thus, in one preferred embodiment, the first and second members 232, 234 are coiled wire that can be longitudinally retracted (i.e., coiled upon itself) to provide a reduced overall length. The connector 236 is rigidly connected at opposite ends thereof to the first and second members 232, 234. In this regard, the connector 236 can be a rigid ring or post that establishes a permanent spacing between the first and second members 232, 234. Alternatively, the connector 236 can include a flexible component (e.g., a thread) that is secured to the first and second members 232, 234 in conjunction with a spacer component (e.g., a ring) that establishes a minimum spacing between the first and second members 232, 234.

Regardless of the exact design, the occlusion device 230 is provided as a unitary structure prior to deployment. That is to say, prior to deployment, the first and second members 232, 234 are permanently attached to at least a portion of the connector 236. The contractible or retractable nature of the first and second members 232, 234 facilitates placement of the entire occlusion device 230 within a cannula (not shown) that otherwise maintains the first and second members 232, 234 in the retracted position prior to deployment. The cannula is then inserted through the anulus defect 44 (FIG. 2) such that a distal end thereof is positioned within the nucleus cavity 42 (FIG. 2). The occlusion device 230 is then directed distally such that the first member 232 is released from the cannula and into the nucleus cavity 42. Once released, the first member 232 self-expands to the deployed state of FIG. 10. The cannula is then removed from the nucleus cavity 42, such that the second member 234 is released from the cannula and self-expands to the deployed state of FIG. 10, at an outside of the anulus 34. The connector 236 establishes a spacing between the first and second members 232, 234, with the occlusion device 230 being secured to opposite sides of the anulus 34 (FIG. 2) in the region of the defect 44.

Figure 11:
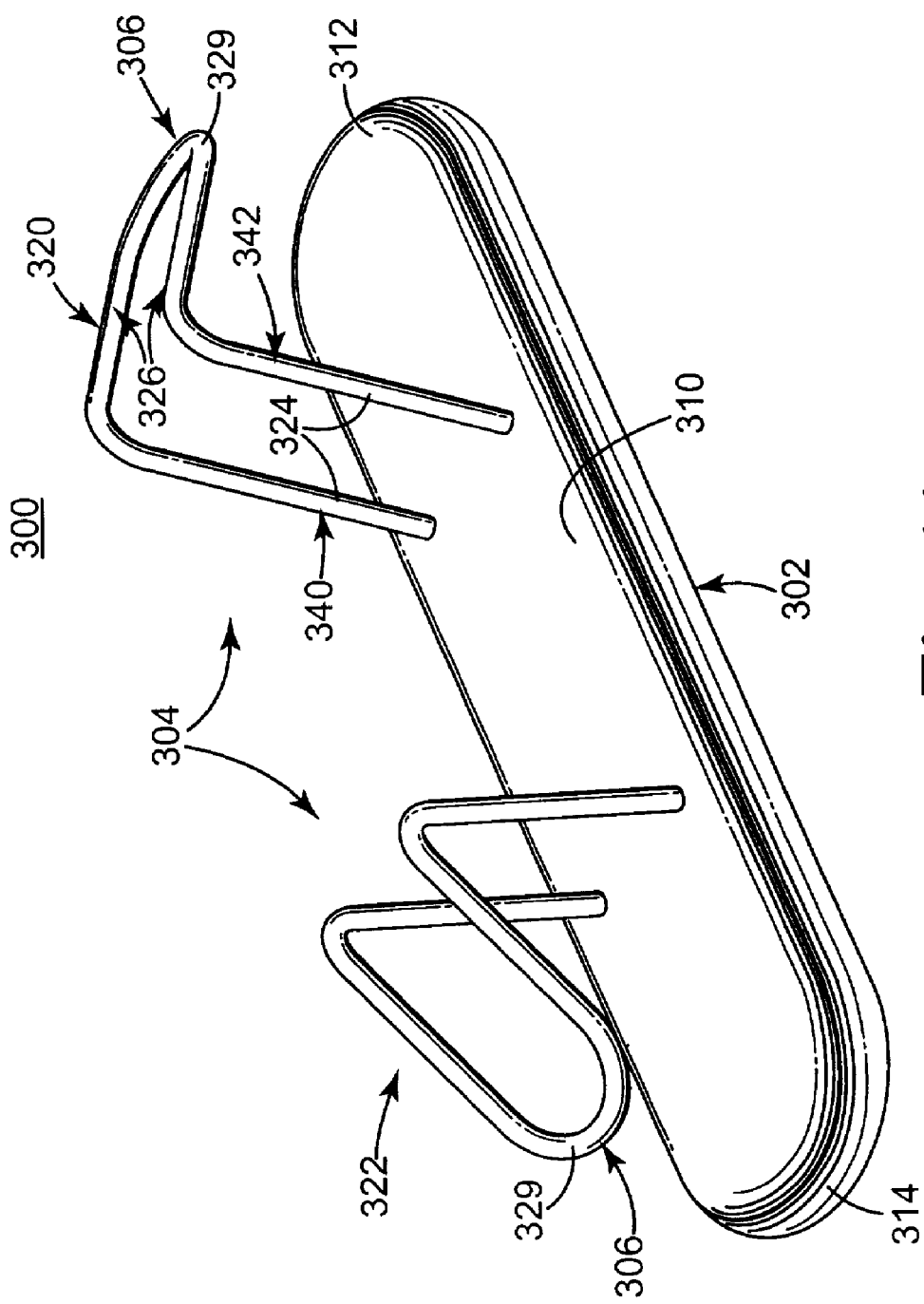
FIG. 11 is a perspective view of another alternative embodiment occlusion device in accordance with the present invention.

Yet another alternative embodiment occlusion device 300 is shown in FIG. 11. The occlusion device 300 includes a plate 302 and a retention component 304. The retention component 304 extends from the plate 302 and defines an anulus engagement portion 306 (referenced generally). In this regard, the retention component 304 is rigid yet deflectable relative to the plate 302. As described in greater detail below, the retention component 304 facilitates securing of the occlusion device 300 to an anulus (not shown) such that the anulus engagement portion 306 and the plate 302 are biased into secure contact with the anulus upon final deployment.

The plate 302 is an elongated body that defines an inner or anulus contact face 310 extending between opposing ends 312, 314. In at least a relaxed or deployed state of FIG. 11, the anulus contact face 310 is preferably planar, having a length greater than a length of the anulus defect being repaired; in one embodiment, the anulus contact face 310 has a length on the order of 10–30 mm in length. Further, the plate 302 has a height that approximates an expected height of the anulus being repaired, preferably on the order of 5–15 mm. Finally, the plate 302 is preferably formed from a strong yet resilient, biocompatible material, that allows the plate 302 to at least partially fold onto itself during an implant procedure and, following implant, return to the relatively flat shape illustrated in FIG. 11, as described below. In one preferred embodiment, the plate 302 is defined by a plastic, such as polyethylene, molded over a continuous wire (described below) that otherwise forms the retention component 304. With this one preferred construction, actuation of the retention component 304 (e.g., collapsing thereof) is translated to the plate 302.

The retention component 304 extends from the contact face 310 of the plate 302, and is preferably comprised of first and second arms 320, 322. The arms 320, 322 are preferably identical, and are centered relative to the opposing ends 312, 314. More particularly, a spacing between the first arm 320 and the opposing end 312 is preferably identical to a spacing between the second arm 322 and the end 314. With additional reference to FIG. 12, preferably the arms 320, 322 are generally L-shaped, each defining a first section 324 and a second section 326. The first section 324 extends from the contact face 310 (from an extension point referenced generally at 328) in an outward fashion. The second section 326 extends from the first section 324, terminating in an arm end 329, and defines an anulus contact surface 330 at an interior side thereof. The anulus contact surfaces 330 of the arms 320, 322 combine to define the anulus engagement portion 306 previously described.

Figure 12:
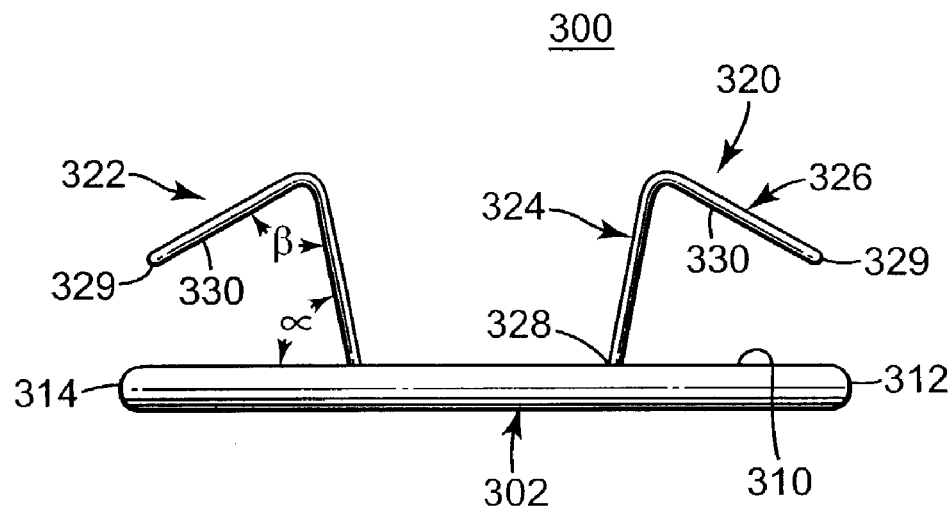
FIG. 12 is a side view of the occlusion device of FIG. 11.

As a point of reference, the arms 320, 322 are depicted in FIGS. 11 and 12 in an unconstrained or relaxed state. As described below, the arms 320, 322 are preferably resiliently deflectable relative to the plate 302, capable of being collapsed toward one another and the contact face 310 in an insertion state. Finally, depending upon a thickness of the anulus (not shown) to which the occlusion device 300 is secured, the arms 320, 322 may define deviations in angular relationships in a deployed state relative to the relaxed state of FIGS. 11 and 12. For example, and as described in greater detail below, the second section 326 of each arm 320, 322 will preferably deflect upon final deployment to be flush with the anulus (not shown). The following description of preferred dimensions/orientations is with respect to the occlusion device 300 in the relaxed state.

In the unconstrained or relaxed state of FIGS. 11 and 12, the first section 324 is canted toward the corresponding end 312 or 314, defining an angle α relative to a plane of the contact face 310. That is to say, the first section 324 of the first arm 320 is canted toward the end 312, whereas the first section 324 of the second arm 322 is canted toward the end 314. In this regard, the angle α is preferably in the range of 70°–89°; more preferably 75°–85°; most preferably approximately 80°. By preferably defining an acute angle between the respective first section 324 and the contact face 310, the arms 320, 322 can accommodate varying anuli thicknesses as described below.

The second section 326 preferably extends at an angle from the first section 324, inwardly toward the contact face 310. A radius of a curvature is preferably defined at the transition of the first section 324 to the second section 326. This curvature facilitates deflection of the second section 326 relative to the first section 324, and is preferably at least 0.020 inch, more preferably at least 0.040 inch. In this regard, orientation of the second section 326 relative to the first section 324 preferably defines an included angle β in the range of 50°–70°; more preferably 55°–65°; most preferably approximately 60°.

The above-described construction of the arms 320, 322 extends the respective arm ends 329/anulus contact surfaces 330 toward the contact face 310. In particular, in the relaxed state of FIGS. 11 and 12, a relaxed state spacing S is defined between each arm end 329 and the contact face 310. Absent any material being inserted between the contact face 310 and the arm ends 329 (e.g., prior to implant), the relaxed state spacing S is slightly smaller than an expected thickness of an anulus. Because the arms 320, 322 are deflectable, the respective arm ends 329, and thus the respective anulus contact surfaces 330, can be deflected relative to the inner face 310 at a distance greater than the relaxed state spacing S; for example when the occlusion device 300 is applied to an anulus (not shown) having a thickness greater than the relaxed state spacing S. Under these conditions, the second section 326 deflects relative to the corresponding first section 324 (i.e., an increase in the included angle β). However, an inherent rigidity of the arms 320, 322 creates compression or inward force on the respective arm ends 329/engagement surfaces 330 relative to the contact face 310. As such, when the occlusion device 300 is deployed to an anulus having a thickness greater than the relaxed state spacing S, the arms 320, 322 effectively "pinch" the anulus material between the contact face 310 and the corresponding arm ends 329/engagement surface 330.

Figure 13:
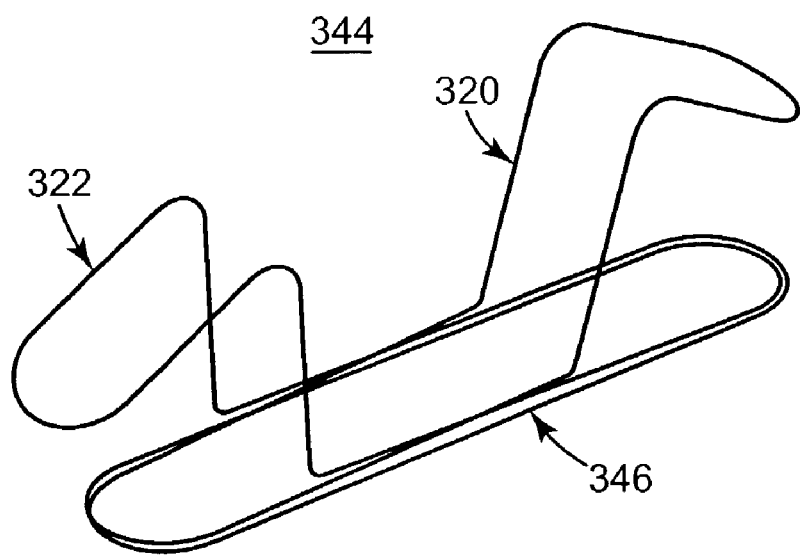
FIG. 13 is a perspective view of a continuous wire portion of the device of FIG. 11.

The preferred rigid yet deflectable nature of the arms 320, 322 is preferably achieved by forming each of the arms 320, 322 from a continuous, biocompatible wire. As best shown in FIG. 11, the wire defines opposing segments 340, 342 otherwise emerging or extending from the contact face 310 and combining to form the first section 324. The opposing segments 340, 342 further combine to define the second section 326, connecting at the arm ends 329, such that the wire defines a loop. In an even more preferred embodiment, a single length of wire forms both of the arms 320, 322, as well as an internal frame for the plate 302. For example, FIG. 13 illustrates a continuous, looped wire 344 defining the arms 320, 322 and a base frame 346. With this preferred embodiment, the plate 302 (FIG. 11) is formed by molding an appropriate material (e.g., polyethylene) over the base frame 346. Following the molding operation, the arms 320, 322 emerge from the molded plate material. Alternatively, other constructions can be employed for the first and second arms 320, 322, such as a separate, integrally formed body for each arm 320 and 322 that is otherwise attached to the plate 302.

Figure 14:
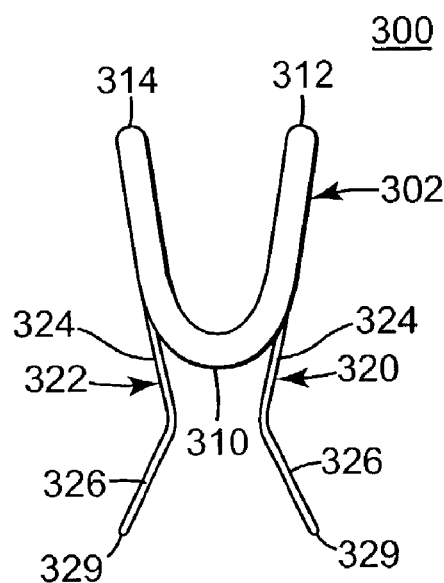
FIG. 14 is a side view of the occlusion device of FIG. 11 in a collapsed state.

As previously described, the arms 320, 322 are rigid yet resilient to deflect and accommodate varying anuli thicknesses. In an even more preferred embodiment, the arms 320, 322 are configured to be deflectable to a compressed or insertion state of FIG. 14 that further illustrates the preferred flexible nature of the plate 302. With this construction, the arms 320, 322 are collapsible toward one another and the contact face 310, such that a spacing between the respective anulus contact surfaces 330 is greatly reduced. Further, the first sections 324 essentially conform to the contact face 310 of the plate 302, and the plate 302 is folded onto itself. In this insertion state, then, the occlusion device 300 is highly streamlined and can be inserted within a delivery tube otherwise used to deploy the occlusion device 300 as described below.

In a preferred embodiment whereby the arms 320, 322 are formed by a continuous wire, a material having super elastic properties is employed, such as a nickel/titanium alloy (NiTi). A coating, such as hyaluronic acid, is further preferably applied to the arms 320, 322. Regardless, with this one preferred wire material, the retention component 304 can be collapsed to the insertion state of FIG. 14. Once released, the arms 320, 322 recover to the original, relaxed state of FIGS. 11 and 12 via the super elastic properties of the wire. In a preferred embodiment, the wire forming the arms 320, 322, respectively, is a NiTi material having a diameter in the range of 0.01–0.03 inch; more preferably 0.02 inch. It has been surprisingly been found that this material selection and diameter provide acceptable stiffness and shape retention characteristics for securing the occlusion device 300 to a human spinal disc anulus.

Figure 15A:
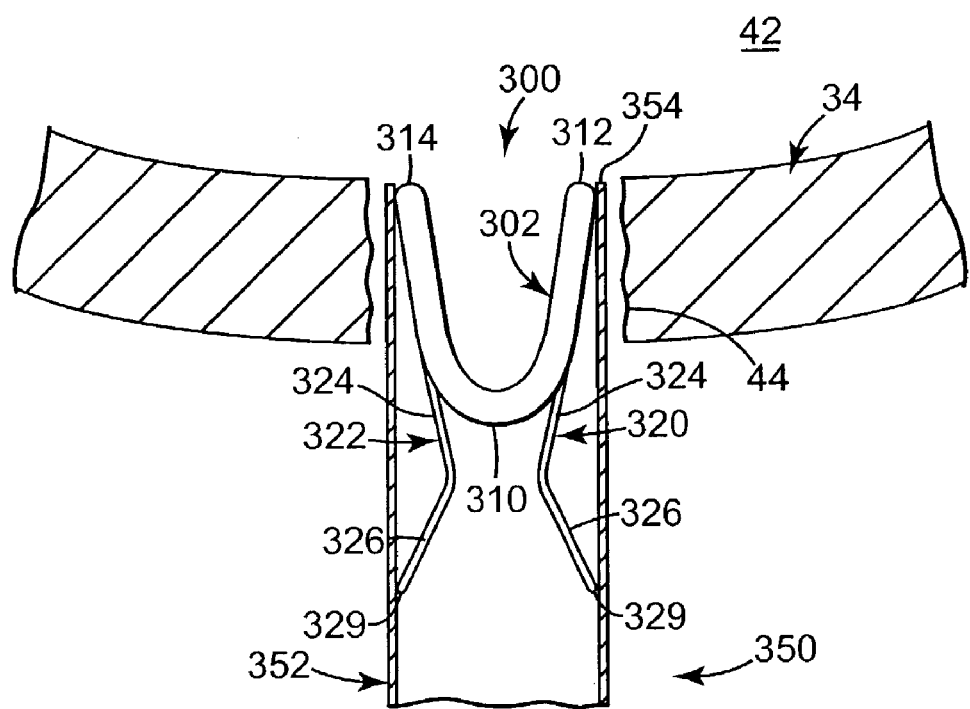
FIGS. 15A–15C are top, sectional views of a portion of the disc space of FIG. 2 illustrating implantation of the occlusion device of FIG. 11.
Figure 15B:
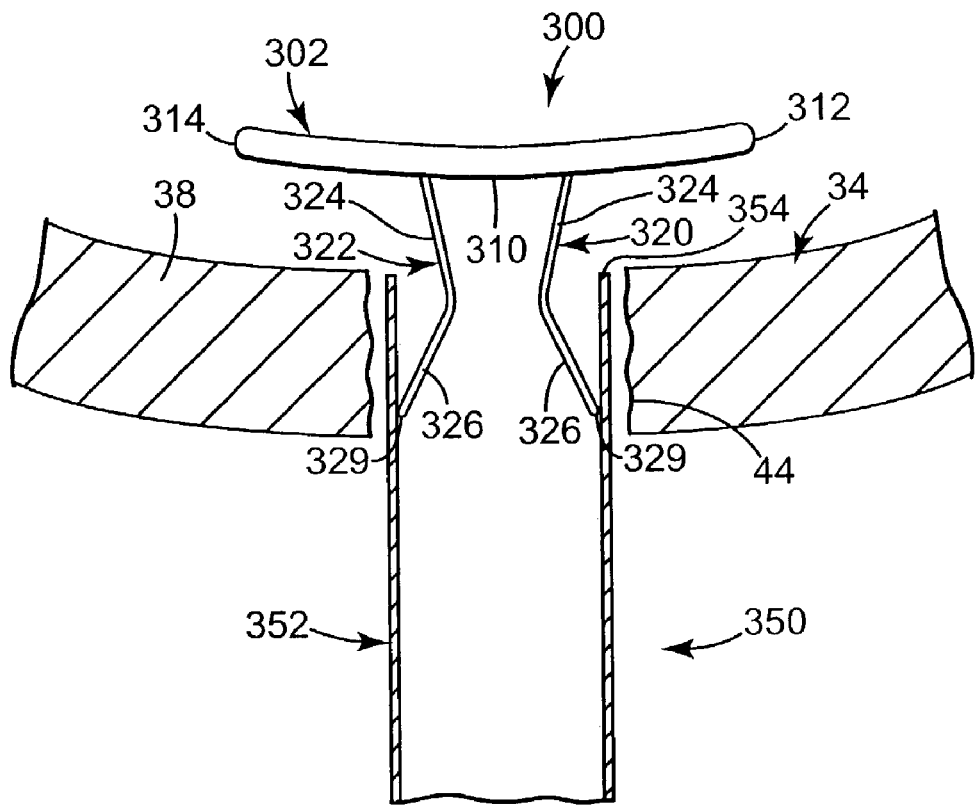
Figure 15C:
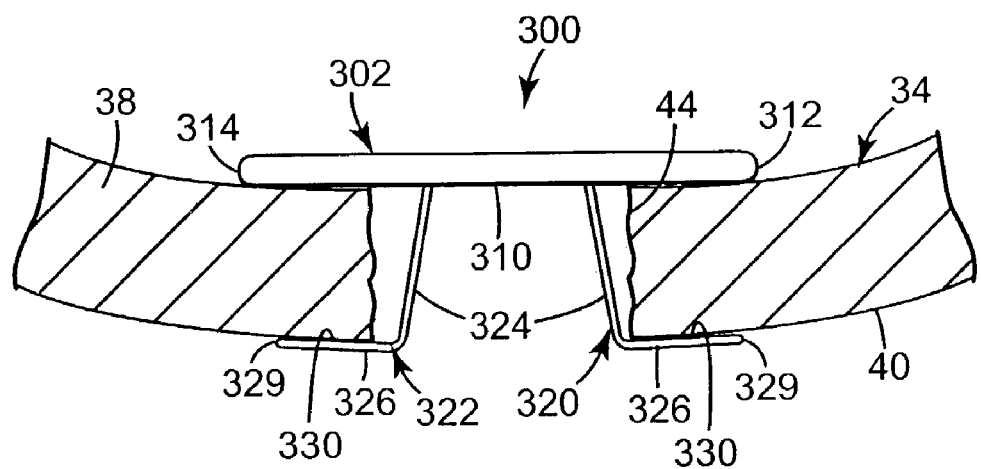

With reference to FIGS. 15A–15C, the occlusion device 300 is deployed to occlude the defect 44 in the anulus 34. In a preferred embodiment, the occlusion device 300 is, prior to implant, retained in an insertion state by an insertion tool 350 (shown generally in FIGS. 15A and 15B). The insertion tool 350 includes a delivery tube 352 adapted to slidably retain the occlusion device 300 in the collapsed/insertion state of FIG. 15A. In particular, internal features (not shown) of the insertion tool 350 initially grasp and slidably retain the arm ends 329/anulus contact surfaces 330 of the arms 320, 322, respectively, and deflect or collapse the arms 320, 322 toward one another. With the one preferred construction whereby a continuous wire forms the arms 320, 322 and the plate 302 is formed by plastic molded over an internal frame 346 (FIG. 13), forcing the arms 320, 322 toward one another causes the plate 302 to fold onto itself (i.e., the ends 312, 314 are drawn toward one another) such that the plate 302 can be retained within the delivery tube 352. With alternative constructions, a more direct force on the plate 302 may be required to achieve the folded position of FIG. 15A. Regardless, once at least partially folded, the plate 302 is readily inserted within the delivering tube 352, and positioned near a distal end 354 thereof. The tube 352 is then directed through the defect 44, such that the distal end 354 is within the nucleus cavity 42.

As shown in FIG. 15A, the plate 302, in the insertion or collapsed state, is within the confines of the anulus 34. The occlusion device 300 is then advanced distally until the plate 302 is released from the distal end 354 of the delivery tube 352. Once released, the plate 302 will at least partially recover or return to its unfolded or relaxed position, as shown in FIG. 15B, preferably due to a super elastic characteristic of the plate 302. The delivery tube 352 is then retracted proximally until the contact face 310 contacts the interior surface 38 of the anulus 34.

The delivery tube 352 is further retracted, with contact between the plate 302 and the anulus 34 preventing further movement/retraction of the occlusion device 300 relative to the delivery tube 352. FIG. 15C illustrates the occlusion device 300 fully released from the delivery tube 352 (FIG. 15B). The plate 302 is fully deployed within the cavity 42 (FIG. 2) such that the contact face 310 faces the interior surface 38 of the anulus 34 at the defect 44. The retention component 304 is deployed such that the anulus engagement portion 306 contacts the exterior surface 40 of the anulus 34, with the anulus contact surfaces 330 being positioned at opposite sides of the defect 44. More particularly, the arms 320, 322 recover or self-deploy to the deployed position of FIG. 15C, whereby the respective anulus contact surfaces 330 contact the exterior surface 40 of the anulus 34. In this regard, a thickness of the anulus 34 is greater than the relaxed state spacing S in FIG. 12, such that the arms ends 329 are forced away from the plate 302. While the arms 320, 322 are deflectable so as to accommodate the anulus thickness, the arms 320, 322 are sufficiently rigid such that the arm ends 329 bear against the exterior surface 40, in turn biasing the plate 302 into engagement with the interior surface 38. In a preferred embodiment, due to an inherent rigidity and canting of the arms 320, 322, the arms ends 329 subside slightly into the anulus 34 tissue. As a result, the anulus 34 is "pinched" between the respective arm ends 329 and the plate 302. Further, the anulus contact surfaces 330 are relatively flush against exterior surface 40, such that the respective second sections 326 are oriented as closely as possible to the anulus 34. This positioning, in turn, minimizes the potential for undesirable contact between the second sections 326 and the spinal cord (not shown).

The spinal disc anulus occlusion device and related method of use of the present invention provides a marked improvement over previous designs. Unlike conventional techniques of suturing an anulus plug or flap to the anulus, the present invention establishes a strong mechanical closure/barrier to the anulus defect. This barrier maintains its position relative to the anulus in response to the normal loads placed upon the disc space, and thus will not unexpectedly dislodge. When provided in conjunction with a prosthetic disc nucleus implant device, the occlusion device of the present invention stabilizes the anulus defect and prevents extrusion or expulsion of the implanted prosthesis.

Although the present invention has been described with reference to preferred embodiments, workers skilled in the art will recognize that changes can be made in form and detail without departing from the spirit and scope of the present invention.

What is claimed is:

1. A method of occluding a defect in a spinal disc anulus including an interior surface and an exterior surface, and defining an internal cavity, the method comprising:

providing an occlusion device including a plate and a retention component extending from an anulus contact face of the plate and terminating in an anulus engagement portion;

deploying the plate within the internal cavity such that the contact face of the plate faces the interior surface of the anulus in a region of the defect; and deploying the retention component such that the anulus engagement portion contacts the exterior surface of the anulus adjacent the defect characterized by the anulus engagement portion not projecting through a thickness of the annulus adjacent the defect;

wherein upon deployment, the retention component biases the plate into engagement with the anulus, thereby securing the occlusion device to the anulus.

2. The method of claim 1, wherein the plate has a length greater than a length of the defect.

3. The method of claim 1, wherein the retention component includes first and second oppositely extending arms each terminating in an arm end, and further wherein deploying the retention component includes:

positioning the arm end of the first arm along the anulus adjacent a first side of the defect; and positioning the arm end of the second arm adjacent an opposite side of the defect.

4. The method of claim 3, wherein the arms are deflectable relative to the plate from a collapsed state to a relaxed state, and further wherein deploying the retention device includes:

forcing the arms to the collapsed state prior to the step of deploying the plate; and releasing the collapsing force from the arms such that the arms self-transition toward the relaxed state.

5. The method of claim 4, wherein the plate is deflectable from the collapsed state in which the plate is folded onto itself and the relaxed state in which the plate is substantially planar, and further wherein deploying the plate includes:

inserting the plate, in the collapsed state, into the internal cavity; and releasing the collapsing force from the plate such that the plate self-transitions toward the relaxed state.

6. The method of claim 3, wherein the arms are configured such that a distance between the respective arm ends and the plate is variable, and further wherein deploying the retention device includes:

deflecting the arms relative to the plate to accommodate a thickness of the anulus.

7. The method of claim 3, wherein deploying the retention component includes:

forcing the arm ends into the anulus tissue.

8. The method of claim 3, wherein each of the arms includes a first section extending from the plate and a second section extending from the first section, and further wherein deploying the retention component includes:

positioning the respective second sections to be substantially flush with the exterior surface of the anulus.

9. The method of claim 1, wherein deploying the plate includes passing the plate through a thickness of the anulus.

10. The method of claim 1, wherein deploying the plate includes deploying an entirety of the plate within the internal cavity.

11. The method of claim 1, wherein deploying the plate includes contacting the inner surface of the anulus with opposing ends of the plate.

12. The method of claim 1, wherein the inner surface of the anulus is defined by the anulus apart from any surface that otherwise defines the defect, and further wherein the plate contacts the inner surface.

13. A method of implanting a prosthetic spinal disc nucleus into a nucleus cavity defined by an anulus having an interior surface and an exterior surface, the method comprising:

creating an opening through the anulus;

inserting a prosthetic spinal disc nucleus into the nucleus cavity through the opening;

providing an occlusion device including a plate and a retention component extending from an anulus contact face of the plate, the retention component terminating in an anulus engagement portion;

deploying the plate into the nucleus cavity in a region of the opening such that the contact face of the plate faces the interior surface of the anulus;

deploying the retention component such that the anulus engagement portion contacts the exterior surface of the anulus adjacent the defect and does not contact the interior surface of the anulus adjacent the defect; and securing the occlusion device to the anulus via a compression force between the anulus engagement portion and the plate such that the occlusion device rigidly resists expulsion of at least a portion of the prosthetic spinal disc nucleus back through the opening.

* * * * *